United States Patent [19]
Rakitsch et al.

[11] Patent Number: 5,587,796
[45] Date of Patent: Dec. 24, 1996

[54] PHOTOELECTRIC MEASURING HEAD FOR THE CONTACTLESS SCANNING OF MEASURING FIELDS ON A PRINTING SHEET WITH AN AIR PERMEABLE ANNULAR DISK

[75] Inventors: Peter Rakitsch, Moosburg; Hans Zehentbauer, Germering, both of Germany

[73] Assignee: MAN Roland Druckmaschinen AG, Germany

[21] Appl. No.: 361,597

[22] Filed: Dec. 22, 1994

[30] Foreign Application Priority Data

Dec. 22, 1993 [DE] Germany ............... 43 43 810.5

[51] Int. Cl.⁶ .................. G01N 21/55; G01J 3/46
[52] U.S. Cl. ............................. 356/445; 356/425
[58] Field of Search .................. 356/445–448, 356/375, 425; 250/559.01, 559.04, 559.16, 559.4, 559.44

[56] References Cited

U.S. PATENT DOCUMENTS

| | | | |
|---|---|---|---|
| 2,683,635 | 7/1954 | Wilcox. | |
| 3,830,505 | 8/1974 | Rabinow | 369/224 |
| 4,606,633 | 8/1986 | Jeschke et al. | 356/445 |
| 4,710,912 | 12/1987 | Greene et al. | 369/218 |
| 4,824,248 | 4/1989 | Neumann | 356/445 |
| 4,884,889 | 12/1989 | Beckwith, Jr. | 356/375 |
| 4,892,407 | 1/1990 | McMurtry et al. | 356/375 |
| 4,927,766 | 5/1990 | Auerbach et al. | 356/445 |
| 5,126,648 | 6/1992 | Jacobs | 318/640 |
| 5,208,655 | 5/1993 | Cox et al. | 356/445 |

FOREIGN PATENT DOCUMENTS

| | | |
|---|---|---|
| 1298899 | 3/1970 | Germany. |
| 3110712A1 | 9/1982 | Germany. |
| 260032A1 | 9/1988 | Germany. |

Primary Examiner—Frank Gonzalez
Assistant Examiner—Jason D. Eisenberg
Attorney, Agent, or Firm—Leydig, Voit & Mayer, Ltd.

[57] ABSTRACT

A photoelectric measuring head for the contactless scanning of measurement regions, particularly of measurement fields on a printing sheet resting flat. The measuring head having outlet orifices for compressed air on its underside to generated an air cushion between the measuring head and the printing sheet. A measuring head of this kind, suspended on an air cushion provides for high stability, and the least possible distance from the base. This is achieved in that the outlet orifice for the compressed air are formed from a plate which, by virtue of a microporous structure, is air-permeable.

7 Claims, 3 Drawing Sheets

PHOTOELECTRIC MEASURING HEAD FOR THE CONTACTLESS SCANNING OF MEASURING FIELDS ON A PRINTING SHEET WITH AN AIR PERMEABLE ANNULAR DISK

BACKGROUND OF THE INVENTION

1. Field of the Invention

The invention relates to a photoelectric measuring head, and more particularly, to a photoelectric measuring head for the contactless scanning of measurement regions.

2. Discussion of the Prior Art

In the graphics industry, photoelectric measuring heads are utilized for recording the reflectances of test regions on a a printed sheet, particularly by the direct-light method. The photoelectric measuring head can, in particular, be designed as a spectral color-measuring head, as a three-range color-measuring head or as a densitometer measuring head. The measurement regions of the printed sheet are, for example, extra co-printed measurement fields which either are arranged in a line in the form of a print-checking strip, or are distributed arbitrarily over the format or around so-called pictorially important locations of the subject. The use of a photoelectric measuring head in the case of printed products which have just been extracted from the printing machine is particularly critical, since the ink or the applied varnish is still fresh, and smudging of the ink or the varnish must be absolutely avoided.

DD 260,032 A1 discloses a spectral measuring head in the form of a densitometer which is displacable via slide guides in the x and y direction and parallel to the plane of a sheet which is resting on a base. Air-outlet orifices, through which compressed air is blown out, are arranged on the underside of the measuring head, in other words on the side which confronts the article to be measured. An air cushion thus builds up and supports the measuring head in suspension above the surface to be measured. Essentially, the measuring head is supported counter to the weight of the latter above the surface to be measured and does not contact the surface, thereby preventing any smudging. Furthermore, the measuring head is vertically displacable and is connected in an articulated manner to the device guiding it in the x–y plane.

In this known measuring head, in order to generate the supporting air cushion, bores, via which the compressed air emerges, are arranged in a uniform distribution along the outer edge of the underside of the measuring head. A problem associated with this type of arrangement is that the supply of compressed air to the corresponding air-outlet bores must be equally distributed to the bores. Essentially, it is necessary to ensure that the same quantity of air per unit time is blown out via each outlet bore. If this is not the case, particularly when this occurs on diametrically opposite sides, a tendency of the measuring head to tilt can arise. The compressed air emerging at each bore flows via a relatively large cross-section at a very high outlet velocity, so that eddies are generated. The eddies of adjacent outlet orifices can influence one another so that, under certain circumstances, the air cushion supporting the measuring head is set into vibration. The distance, between the measuring optics and the surface to be measured must be kept constant. If the separation distance is not maintained at a constant value, the measuring accuracy is impaired. Accordingly, the vibration causes changes in the distance and thereby produces inaccuracies in the measurement.

SUMMARY OF THE INVENTION

The present invention is directed to a photoelectric measuring head for scanning of measurement fields on a printing sheet in such a way that the measuring head can be supported at the least possible distance above the base in a stable manner by means of an air cushion. The photoelectric measuring head comprises light generating means for directing light toward the target sheet, a photoelectric receiver for capturing light reflected from the printing sheet, at least one annular chamber for holding and distributing compressed air, and an air permeable plate mounted below and communicating with the at least one annular chamber. The air permeable plate providing for an evenly distributed air flow at a predetermined flow rate for generating the air cushion between the measuring head and the printing sheet.

According to the present invention, the outlet orifices for the compressed air are formed from a plate which, by virtue of a microporous structure, is air-permeable. In particular, this microporous, air-permeable plate consists of a sintered metal. The air permeable porous structure has openings which are of a size in the range of hundredths of a millimeter, thereby ensuring an even air flow distribution.

Because of the multiplicity of micronozzles, i.e., the pores distributed randomly over the plate surface, the generation of a preferential direction of the outflowing air and the associated generation of torques which would entail a tilting of the measuring head is prevented. The compressed air emerges through this plate with a turbulent flow in the microscopic range and with a laminar flow in the macroscopic range. In particular, by means of a plate of this kind, air-permeable by virtue of a micro-porous structure, a stable and uniform supporting pressure can be generated over its surface confronting the base upon which the printing sheet is mounted. The measuring head, which is supported via the air cushion generated by this plate, can be held in a stable manner at the least possible distance (approx. 0.2 mm) from the base.

In particular, the plate, air-permeable by virtue of the microporous structure, can be designed as an annular disc which is formed concentrically relative to the measuring optics on the underside of the measuring head. A uniform flow-off of the emerging compressed air in the radial direction is thus obtained. The measuring optics are thus advantageously protected against the deposition of dust and the like.

The photoelectric measuring head according to the invention may be used advantageously in a measuring system which can be moved both in an axial direction and in a plane. At the same time, it is particularly advantageous if the measuring head according to the present invention is suspended on the movement device via an extremely smooth-running linear guide. A so-called cross-roller guide is employed here in a particularly advantageous manor. This is characterized in that cylindrical rollers are arranged between the guide parts mounted on the measuring head and the guide parts of the movement suspension, in such a way that the axes of one particular group of rollers lie in one plane and this plane intersects at a substantially acute angle another plane passing through the axes of another group of cylindrical rollers.

BRIEF DESCRIPTION OF DRAWINGS

There follows an explanation of an exemplary embodiment of the invention with reference to the drawing. In the drawing.

DETAILED DESCRIPTION OF THE PREFERRED EMBODIMENTS

Figure 1:
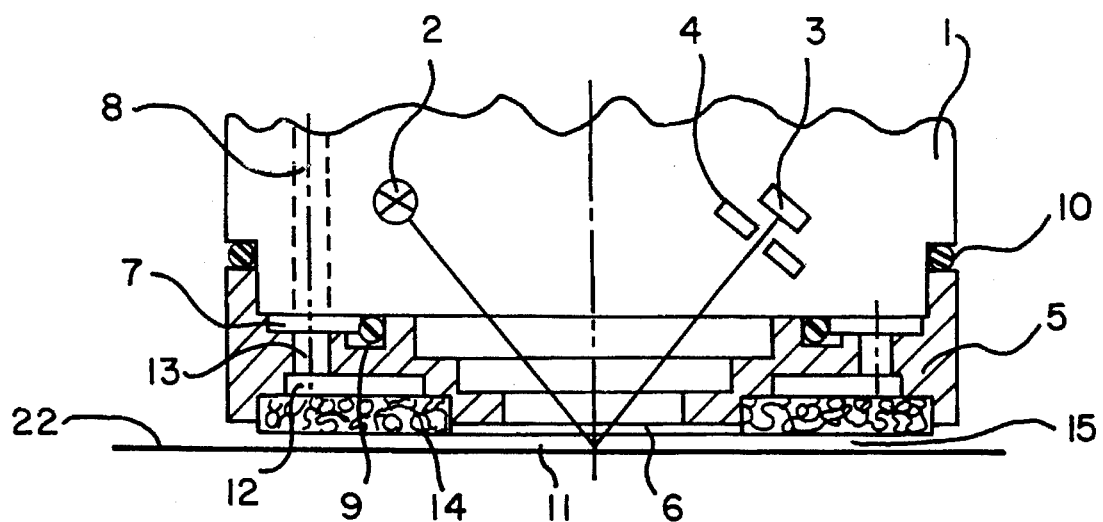
FIG. 1 is a sectional view of the photoelectric measuring head of the present invention.

FIG. 1 illustrates, in section, a measuring head 1 with a light generating means 2 arranged therein and with a photoelectric receiver 3 preceded by a diaphragm 4. The geometry shown between the light generating means 2 and the photoelectric receiver 3 is purely symbolic. Basically, the light from the light generating means is directed to the particular regions on the printing sheet 22, and the photoelectric receiver 3 captures the light reflected off the printing sheet 22. Placed on the lower surface of the measuring head 1 is a cover 5, in the middle of which a circular orifice 6 is provided as a measuring diaphragm. This orifice 6 widens in steps and, in each case, concentrically relative to the outer-axis of the measuring head 1 in the direction of the optical device consisting of the light generating means 2 and of the photoelectric receiver 3.

An annular chamber 7 extending concentrically relative to the outer-axis of the measuring head 1 is fashioned on the side of the cover 5 confronting the underside of the measuring head 1. This annular chamber 7 may be filled with compressed air via a bore 8 in the measuring head 1 from a source not shown. To ensure that the compressed air introduced into the annular chamber 7 cannot escape, a sealing ring 9, 10 is arranged on each of the two sides of the chamber 7 or on one side of the chamber 7 and in the region between the cover 5 and the measuring head 1.

A further chamber 12 likewise extending concentrically relative to the outer-axis of the measuring head 1 is constructed on the side of the cover 5 confronting the base 11 upon which the printing sheet 22 is positioned. In particular, the chamber 12 likewise has the same rectangular cross-section as the first annular chamber 7. The circular chamber 12 is connected to the first annular chamber 7 via four bores 13 distributed uniformly in a circular pattern extending concentrically relative to the control-axis of the measuring head 1. In an appropriate widening of the chamber 12 in the cover 5, the chamber 12 is closed off relative to the base 11 by means of an annular plate 14 consisting of sintered metal.

The compressed air introduced into the annular chamber 7 via the bore 8 in the measuring head 1 thus passes through the bores 13 into the second annular chamber 12 and therefore emerges uniformly on the underside of the cover 5 over the entire surface of the plate 14. An air cushion 15 is consequently generated between the base 11 and the side of the plate 14 confronting the base 11. This air cushion 15 supports the measuring head 1 counter to the weight of the latter.

The plate 14 is formed from a sintered material, preferably sintered metal, and therefore is a microporous structure. The compressed air is forced through the pores in the plate to generate the air cushion 15. The pores in the plate 14 are of a size in the range of hundredths of a millimeter, thereby ensuring an even air flow distribution. The plate 14 may be constructed as an annular disc which is mounted concentrically relative the measuring optics on the underside of the measuring head. This particular shape provides for a uniform flow-off of the compressed air in the radial direction. In generating this type of flow, the measuring optics are protected against the deposition of dust and the like.

Figure 2:
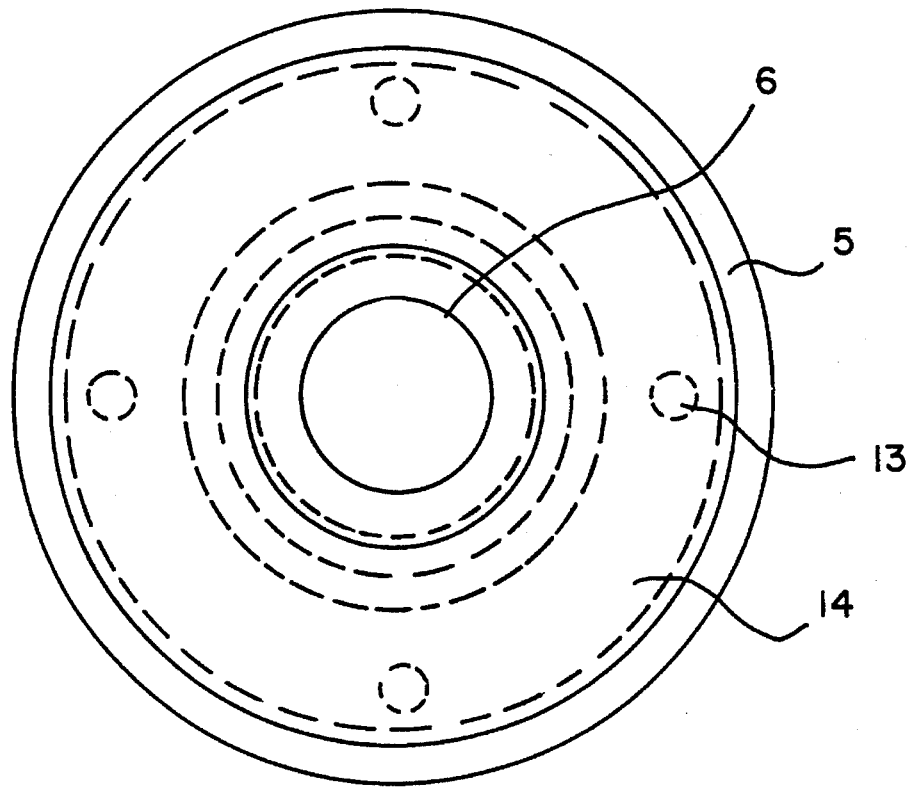
FIG. 2 is a top view of the underside of the photoelectric measuring head of the present invention.

FIG. 2 shows a top view of the underside of the measuring head 1 or of the cover 5. The circular orifice 6 in the cover 5, which is in the middle, and the arrangement of the annular plate 14 concentric thereto are shown in the figure. In this exemplary embodiment, the cover 5 has a circular cross-section and is fastened to the measuring head 1, not shown, and likewise having a circular cross-section, for example via a thread or by means of screws not shown.

Figure 3:
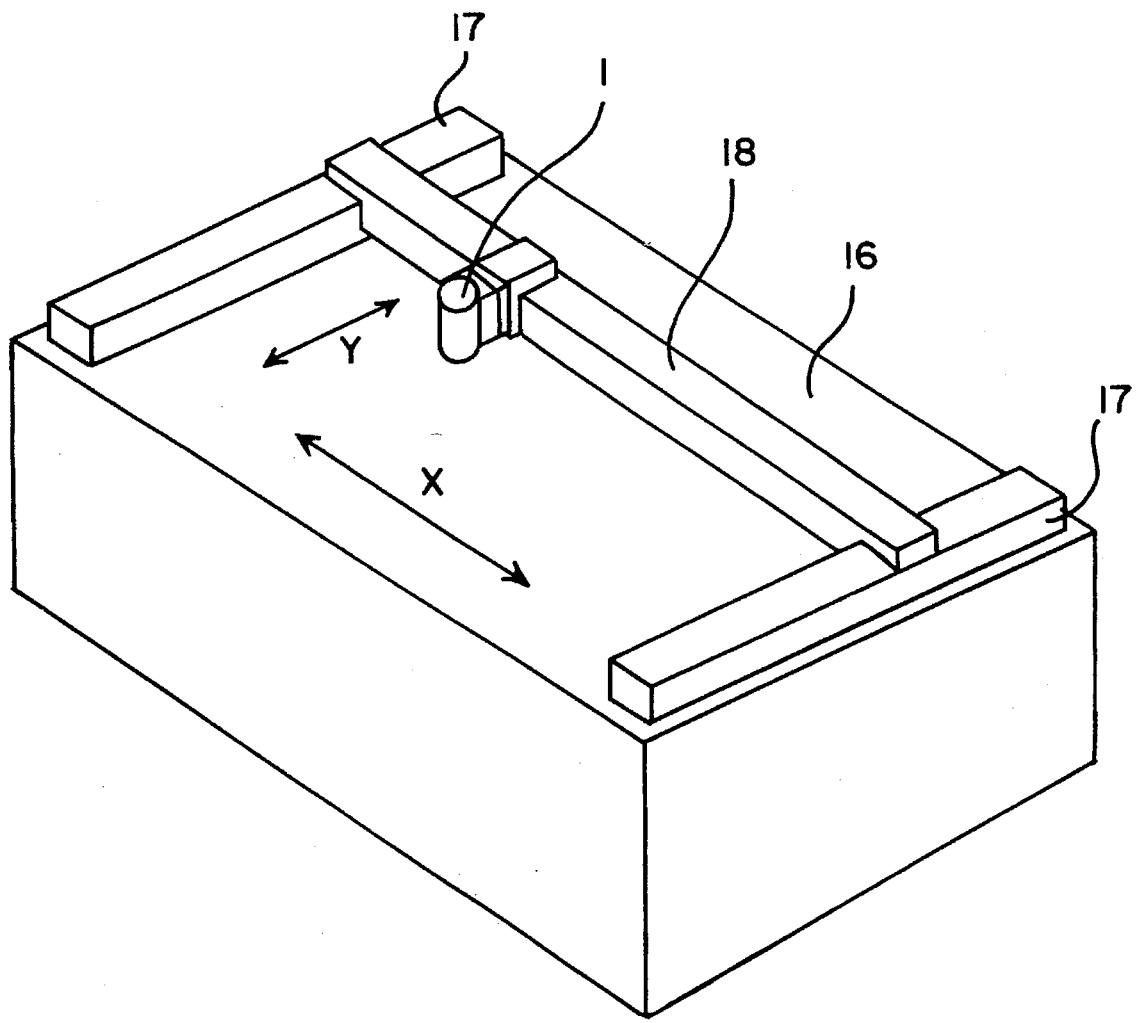
FIG. 3 is a perspective view of a measuring table utilizing the photoelectric measuring head of the present invention.

FIG. 3 illustrates a perspective view of an exemplary measuring table 16 upon which the photoelectric measuring head 1 is utilized. A pair of slide guides 17 are mounted to the upper surface of opposite ends of the measuring table 16. The slide guides 17 are arranged substantially parallel to one another along the outer edges of the measuring table. A bridge 18 is connected between the two parallel slide guides 17. The bridge 18 runs along the parallel slide guides 17 in the Y direction, and the photoelectric measuring head 1 runs along the bridge 18 in the X direction. Accordingly, the photoelectric measuring head 1 is displacable in the X–Y plane by means of the slide guides 17 and the bridge 18.

Figure 4:
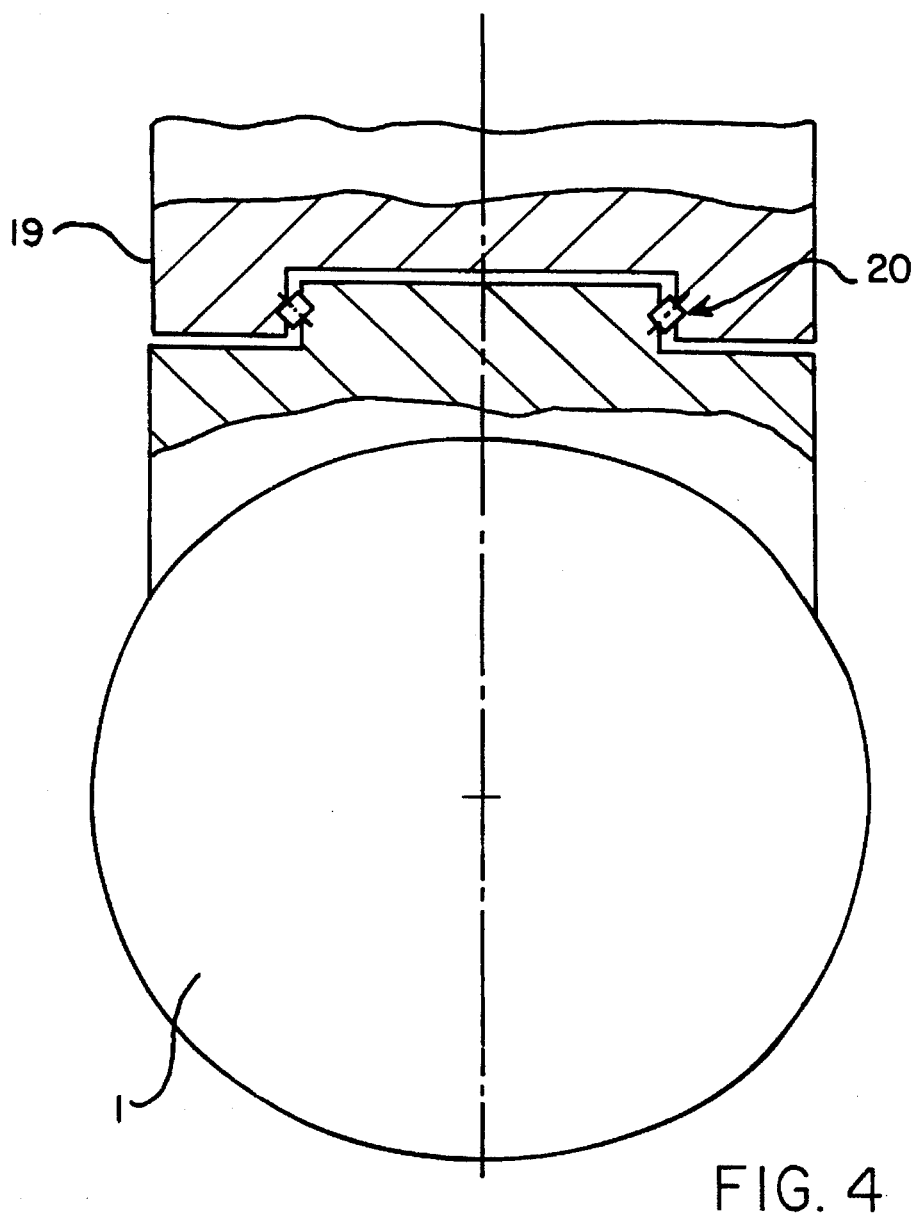
FIG. 4 is a diagrammatic representation of a cross-roller guide for securing the photoelectric measuring head of the present invention.

The photoelectric measuring head 1 is attached to the bridge 18 in a manner so as to move in the X direction and also in the vertical direction by means of the air cushion 15 illustrated in FIG. 1. In order to move in the vertical direction, the photoelectric measuring head 1 may be linked with the bridge 18 by a cross-roller guide 19 as is illustrated in FIG. 4. As illustrated, the cross-roller guide 19 comprises two rows of rollers 20 which facilitate movement in the vertical direction.

The arrangement illustrated in FIG. 4 provides for a very smooth running guide 19. This smooth running guide 19 provides for accurate vertical guidance along with smooth running. Therefore, as a result of a guide 19 with this particular design, the air cushion 15 supporting the photoelectric measuring head 1 does not experience any additional forces.

Figure 5:
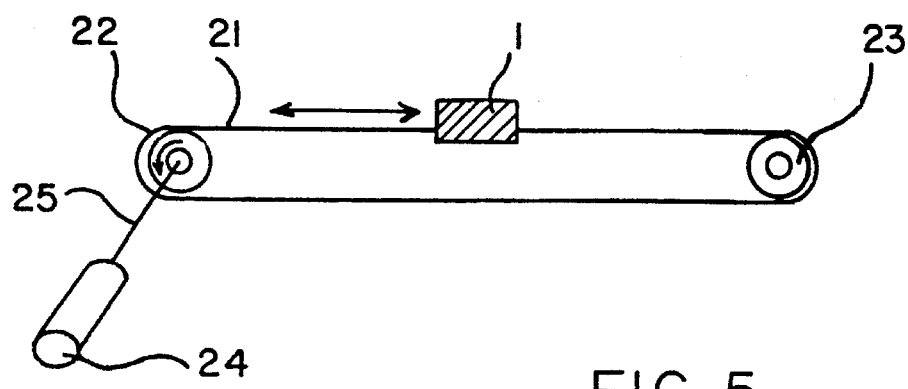
FIG. 5 is a diagrammatic representation of an actuation device in accordance with the present invention.

FIG. 5 illustrates an exemplary embodiment of a simple actuation device for moving the photoelectric measuring head 1 and/or the bridge 18. The actuation device comprises a drive belt 21 and two drive rollers 22 and 23 to which the drive belt 21 is attached. One of the rollers 22 or 23 may be connected to a motor. In the illustrated embodiment, roller 22 is connected to a motor 24 by a drive shaft 25, and the photoelectric measuring head 1 is connected to the drive belt 21. The actuation device may be arranged in the slide guides 17 or in the bridge 18.

Although shown and described is what is believed to be the most practical and preferred embodiments, it is apparent that departures from specific methods and designs described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed:

1. A photoelectric measuring head comprising:

an optical device for scanning measurement fields on a printing sheet, the optical device including a light generating means for directing light to the printing sheet and a photoelectric receiver for capturing light reflected from the printing sheet;

a cover including an orifice in which the optical device is disposed and a measuring diaphragm through which light from the light generating means and light reflected from the printing sheet travels;

at least one annular chamber extending in the cover concentrically relative to a central axis of the photoelectric measuring head such that the annular chamber does not block the measuring diaphragm, and wherein the at least one annular chamber holds and distributes compressed air; and an air permeable annular disc mounted to the cover below the at least one annular chamber and wherein the at least one annular chamber provides the compressed air therein through the air permeabe annular disc providing an evenly distributed air flow at a predetermined flow rate that generates an air cushion between an underside of the cover and the printing sheet, the air permeable annular disc extends from the cover concentrically relative to a central axis of the photoelectric measuring head such that the air permeable annular disc does not block the measuring diaphragm.

2. The photoelectric measuring head according to claim 1, wherein the air permeable annular disc is made from a substance obtained by means of particles sintered together.

3. The photoelectric measuring head according to claim 2, wherein the air permeable annular disc comprises a sintered metal.

4. The photoelectric measuring head according to claim 1, wherein the air permeable annular disc is attached to an underside of the cover.

5. The photoelectric measuring head according to claim 1, further comprising a second annular chamber in the cover, the second annular chamber being connected to the at least one annular chamber via a plurality of evenly distributed conduits.

6. The photoelectric measuring head according to claim 1 wherein the measuring diaphragm comprises a plurality of concentrically arranged orifices in the cover.

7. A measuring table comprising:

first and second slide guides mounted to opposite ends of an upper surface of the measuring table;

a bridge connected between the first and second slide guides;

a photoelectric measuring head, the photoelectric measuring head including:

an optical device for scanning measurement fields on a printing sheet, the optical device including a light generating means for directing light to the printing sheet and a photoelectric receiver for capturing light reflected from the printing sheet;

a cover including an orifice in which the optical device is disposed and a measuring diaphragm through which light from the light generating means and light reflected from the printing sheet travels;

at least one annular chamber extending in the cover concentrically relative to a central axis of the photoelectric measuring head such that the annular chamber does not block the measuring diaphragm, and wherein the at least one annular chamber holds and distributes compressed air; and an air permeable annular disc mounted to the cover below the at least one annular chamber and wherein the at least one annular chamber provides the compressed air therein through the air permeable annular disc providing an evenly distributed air flow at a predetermined flow rate that generates an air cushion between an underside of the cover and the printing sheet, the air permeable annular disc extends from the cover concentrically relative to a central axis of the photoelectric measuring head such that the air permeable annular disc does not block the measuring diaphragm; and an actuation device for moving at least one of the photoelectric measuring head and the bridge.

* * * * *